United States Patent [19]

Papantoniou et al.

[11] Patent Number: 4,595,585
[45] Date of Patent: Jun. 17, 1986

[54] COSMETIC COMPOSITION CONTAINING A POLYCONDENSATE

[75] Inventors: Christos Papantoniou, Montmorency; Jean Mondet, Drancy; Claudine Lapoiriere ex. spouse Vandenbossche, Aulnay-sous-Bois, all of France

[73] Assignee: L'Oreal, Paris, France

[21] Appl. No.: 601,355

[22] Filed: Apr. 17, 1984

[30] Foreign Application Priority Data

Apr. 18, 1983 [FR] France ................. 83 06293
Apr. 19, 1983 [FR] France ................. 83 06365

[51] Int. Cl.⁴ .................... A61K 7/00; A61K 9/00; A61K 7/06
[52] U.S. Cl. ................................ 424/47; 424/70; 424/DIG. 1; 424/DIG. 2
[58] Field of Search ............... 424/DIG. 2, 70, 47, 424/DIG. 1

[56] References Cited

U.S. PATENT DOCUMENTS 3,591,558  7/1971  Brown et al. ................. 528/126

OTHER PUBLICATIONS

Ash, *A Formulary of Cosmetic Preparations,* pp. 103–115 (1977).
*Clinical Toxicology of Commercial Products,* Gleason et al., pp. 102–103 (1969).
Chemical Abstracts, vol. 80, No. 12, Mar. 25, 1974, p. 2, No. 60247x.

*Primary Examiner*—Jerome D. Goldberg
*Assistant Examiner*—Freda L. Abramson
*Attorney, Agent, or Firm*—Cushman, Darby & Cushman

[57] ABSTRACT

A cosmetic composition contains a polycondensate having units of the formula

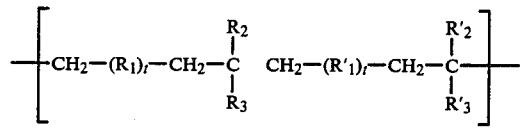

wherein t is 0 or 1. When t=1, $R_1$ and $R'_1$ each independently represent linear or branched alkylene having 1–38 carbon atoms optionally interrupted by —CONH— or —CO—; alkenyl or alkynyl having 2–18 carbon atoms; cycloalkylene having 5–6 carbon atoms; arylene or bis-arylene optionally substituted by alkyl or alkoxy; or a divalent radical of the formula, —CHR'—O—$C_2H_3$(R')—O]$_n$HCR'— wherein n is 0–20 and R' represents hydrogen or methyl, and $R_2$, $R'_2$, $R_3$ and $R'_3$ each independently represent —COOR$_4$, —CN, —CONH$_2$ or —COCH$_3$, wherein $R_4$ represents hydrogen, linear or branched alkyl having 1–18 carbon atoms or cycloalkyl having 5–6 carbon atoms.

5 Claims, No Drawings

COSMETIC COMPOSITION CONTAINING A POLYCONDENSATE

The present invention relates to cosmetic compositions containing, as a polymer, a polycondensate, these compositions being intended, most particularly, for application to the skin, the nails and the hair.

Various polymers are employed as components in a large number of cosmetic compositions, either as the principal component, such as for example in hair lacquers and hair setting lotions, or as a secondary component in such compositions as nail enamels, or as a resin in such other cosmetic compositions as creams, gels or milks so as to improve the texture thereof and to impart good cosmetic properties thereto.

In hair lacquers and hair setting lotions, the polymers must have good lacquering power and impart suppleness to the hair as well as an agreeable aspect, such as softness to the touch.

While such polymers must have a certain degree of hardness they must not be so hard or brittle that they are easily fractured. Otherwise such hard or brittle polymers break into flakes which are generally considered unesthetic.

In nail enamels or polishes, the polymers are essentially intended to form a flexible film exhibiting good adhesion to the nail so that the enamel, once applied, does not break or crumble.

Numerous polymers, having various structures, have been proposed but few of them are capable, with certain minor modifications, of being employed both in aqueous or hydroalcholic compositions such as in hair lacquers or hair setting lotions and in anhydrous compositions, based on a mixture of organic solvents, such as nail enamels.

It has now been found that starting with a certain class of polycondensates, it is possible, by means of certain minor modifications, to obtain polymers exhibiting good solubility properties in water, in organic solvents and in oils.

The present invention thus relates to, as a new industrial product, an aqueous or anhydrous cosmetic composition containing as the principal or secondary component, a polycondensate having units corresponding to the following formula

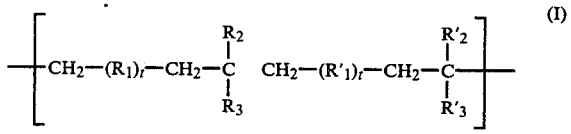

wherein
t is 0 or 1, and
when t=1, $R_1$ and $R'_1$ each independently represent linear or branched alkylene having 1-38 carbon atoms, optionally interrupted by —CONH— or —CO—; alkenyl or alkynyl having 2 to 18 carbon atoms; cycloalkylene having 5 to 6 carbon atoms; arylene or bis-arylene optionally substituted by alkyl or alkoxy; or a divalent radical of the formula, —CHR'—[O—$C_2H_3$(R')O]$_n$HCR'— wherein n is 0–20 and R' represents hydrogen or methyl, $R_2$, $R'_2$, $R_3$ and $R'_3$ each independently represent —COOR$_4$, —CN, —CONH$_2$ or —COCH$_3$, wherein $R_4$ represents hydrogen, linear or branched alkyl having 1-18 carbon atoms or cycloalkyl having 5-6 carbon atoms.

Representative particularly preferred cycloalkylene, arylene and bis-arylene radicals include cyclohexylene, 1,4-dimethylene cyclohexane, phenylene, xylylene, diphenylene, diphenylene methane and 2,2-diphenylene propane.

The polycondensates of the compositions according to the present invention can have generally high molecular weights ranging, for instance, between 400 and 100,000 and preferably between 1,000 and 30,000, measured by osmometry or by light diffusion method or by size exclusion chromatography.

It results from the general formula (I) above, that the polycondensates employed in the cosmetic compositions according to the present invention constitute a compromise between polymers having a linear chain such as those of the polyethylene type and polyfunctional polymers such as polyacrylic acids, polyacrylamides, polyacrylates or even polyacrylonitriles.

It will also be noted that as a function of the meaning of the radicals $R_1$ and $R'_1$, it is possible to regulate at will the distance between the functional radicals especially when they represent alkylene, alkenylene or alkynylene radicals or a divalent radical of the formula, —CHR'—O—[$C_2H_3$(R')—O]$_n$HCR'—.

Depending upon the meaning of $R_2$, $R'_2$, $R_3$ and $R'_3$ radicals selected the polycondensates can be either soluble in water, when these radicals represent carboxylic acid functions, or soluble in organic solvents or oils when these radicals represent ester, nitrile, amide or acetyl functions.

In the compositions according to the present invention, whether aqueous or anhydrous, the amount of the polycondensate of formula (I), such as defined above, is generally between 0.5 and 25 percent by weight based on the total weight of said composition.

When the polycondensates are carriers of amide or carboxylic acid functions (optionally neutralized) they are preferably used in hair lacquers in aerosol form or not, hair setting lotions, hair treating compositions, dye vehicles, shampoos, "rinse" compositions which are applied to the hair after washing the hair with a shampoo.

When the polycondensates are carriers of ester or nitrile functions they are preferably employed in colorless or colored nail enamels.

However, the polycondensates can also be used as secondary components in cosmetic compositions for the skin such as for example in gels, milks, emulsions or masks.

As an example, an aerosol hair lacquer can be produced by packaging in an aerosol container from 0.2 to 8 weight percent of a polycondensate of formula (I), from 6 to 30 weight percent and preferably from 8 to 25 weight percent of an alcohol, the remainder being essentially constituted by a liquified propellant gas under pressure such as dichlorodifluoromethane, trichlorofluoromethane, nitrous oxide or $CO_2$ or mixtures of the above. Preferably the alcohol is ethanol or isopropanol.

Hair lacquers in the form of aqueous, hydroalcoholic or alcoholic solutions can also be sprayed onto the hair using a container fitted with a pump.

Hair setting lotions made in accordance with the present invention can be produced for example by introducing into a hydroalcoholic solution having a titer of 20 to 70% alcohol, from 0.3 to 6% by weight of a polycondensate of formula (I).

In nail enamel compositions according to the present invention the polycondensates of formula (I) are preferably present in an amount between 0.5 and 30 weight percent relative to the total weight of the enamel. In these nail enamel compositions, the polycondensates constitute the film forming resin.

The enamel base is essentially constituted by a solvent system, that is to say, a mixture of conventionally employed organic solvents and/or diluents.

In order to improve the adherence and flexibility of the film, the enamel can also contain from 0.2 to 10 weight percent of at least one plasticizing agent.

Representative plasticizing agents include, for instance, tricresyl phosphate, benzyl benzoate, tributyl phosphate, butyl acetyl ricinoleate, glyceryl acetyl ricinoleate, dibutyl phthalate, butyl glycolate, dioctyl phthalate, butyl stearate, triphenyl phosphate, tributoxyethyl phosphate, triethyl citrate, tributyl citrate, tributyl acetyl citrate, 2-triethyl hexyl acetyl citrate, dibutyl tartrate, ethyl dimethoxy phthalate, di-isobutyl phthalate, diamyl phthalate, camphor, glycerol triacetate, and mixtures thereof.

These enamel compositions can also contain nitrocellulose and principally nitrocellulose of the "RS" or "SS" type and in particular, nitrocellulose type ¼ second RS, nitrocellulose type ½ second RS and nitrocellulose type ¾ second RS.

Preferably in the nail enamel compositions nitrocellulose of the "RS" type is employed.

The solvent system of the nail enamel compositions according to the present invention is one based on volatile organic solvents or mixtures thereof.

Representative solvents which provide relatively short drying times, include, acetone, ethylacetate, butyl acetate, 2-methoxyethyl acetate, methylethyl ketone, methylisobutyl ketone and methylacetate.

The solvent system can also include a diluent and preferably an aromatic organic solvent such as toluene or xylene in an amount generally between 10 and 30 percent relative to the total weight of the enamel.

The enamel composition can also contain other volatile solvents such as ethanol, n-butanol, n-propanol, isopropanol or mixtures thereof, these volatile solvents being more particularly employed when the enamel contains certain quantities of nitrocellulose.

The enamels can be colored and in this case, they contain at least one coloring agent of an organic or inorganic nature.

Representative organic coloring agents include D and C Red 10, 11, 12 and 13, D and C Red 7, D and C Red 5 and 6, D and C Red 34, lakes such as D and C Yellow 5 lake, D and C Red 2 lake. Representative inorganic coloring agents, include titanium dioxide, brown iron oxide, bismuth oxychloride, iron oxide, red iron oxide as well as guanine.

These coloring agents are preferably present in the enamel in an amount between 0.1 and 8 weight percent relative to the total weight of the composition.

Certain ones of the polycondensates used in the compositions according to the invention are known while others are new.

These polycondensates can be obtained either according to the process described in French Pat. No. 1,547,098 or preferably by using a technique called phase transfer catalysis.

According to this particularly preferred technique, the reaction is carried out in the presence of a phase transfer agent such as a quaternary ammonium salt, a "ring ether", a phosphonium salt or a polyethylene glycol in the presence of an alkaline agent, either in an organic medium, or in an aqueous-organic medium.

When the reaction is carried out in an organic medium, the alkaline agent, which is most often sodium or potassium hydroxide, is present in the solid state and the phases are then of the "solid-liquid" type.

On the other hand when the reaction is carried out in an aqueous-organic medium, the alkaline agent is in solution in the aqueous phase and the phases are then of the "liquid-liquid" type.

The preparation of the polycondensates consists in reacting, in the presence of a phase transfer agent, at least one dihalogenated compound on at least one reactant rendered nucleophilic by the presence of a base such as sodium hydroxide or potassium hydroxide at a temperature between 20° and 160° C.

The polycondensation reaction can be carried out in mass or in the presence of an organic solvent, preferably in xylene, toluene, benzene or methylene chloride or even in an aqueous-organic medium, preferably in a water/toluene mixture.

Representative catalysts favoring the polycondensation reaction by phase transfer, include, most particularly, quaternary ammonium salts, principally tetramethylammonium chloride (TMAC), tetraethylammonium chloride (TEAC), tetrabutylammonium chloride (TBAC), benzyltriethylammonium chloride (BTEAC), cetyltrimethylammonium chloride (CTMAC) and tetrabutylammonium hydrogen sulfate (TBAHS).

The amount of quaternary ammonium salts can vary from a few percent relative to the reactants used in the reaction up to an equimolar amount.

It is also possible to use "ring ethers" and in a general manner to use all catalysts for this phase transfer type of polycondensation including those described in the following literature references: "Phase Transfer Catalysis" by C. M. Starks and C. Liotta, Academic Press, 1978, and "Phase Transfer Catalysis in Organic Synthesis", by W. P. Weber and G. W. Gokel, Springe, Verlog 1977.

The dihalogenated compounds can have quite varied structures depending on the meanings of the $R_1$ and $R'_1$ radicals selected. Preferably, the dihalogenated compounds are dibromo or dichloro derivatives and representative preferred ones include principally, 1,6-dibromo hexane, 1,10-dibromo decane, 1,4-dichloro-2-butene, 1,4-dichloro-2-butyne, 1,4-dichloromethyl cyclohexane, 1,4-dichloromethyl benzene, 1,3-dichloromethyl benzene, 1,4-di(2-chloroethyl)benzene, 1,4-di(2-chloroethyl)cyclohexane, 1,1'-di(-chloromethyl) diphenyl, 2,2-bis(4-chloromethyl phenyl) propane and α-ω dichloro-polyoxyethylenes.

Representative nucleophilic reactants particularly appropriate for the polycondensation reaction include diethyl malonate, ditert.butyl malonate, dihexyl malonate, dioctadecyl malonate, ethyl cyanoacetate, tert.butyl acetoacetate and malonitrile.

Using the polycondensates thus obtained with these nucleophilic initial reactants, it is possible to produce other polycondensates of formula (I) carrying different functional groups.

Thus, starting with a polycondensate carrying ester functions, it is possible to produce by hydrolysis polycondensates carrying carboxylic acid functions, the hydrolysis being able to be only partial.

The hydrolysis conditions are those known for converting ester functions into acids. However, in certain instances, in order to avoid complete decarboxylation reaction, the ester functions are preferably hydrolyzed into acid functions in the presence of pure trifluoroacetic acid in an anhydrous medium.

When the polycondensate of formula (I) exhibits free carboxylic acid functions, they can be neutralized by at least one organic or mineral base in an amount between 10 and 100 percent.

Representative mineral or organic bases include, particularly, NaOH, KOH, ammonia, monoethanolamine, diethanolamine, triethanolamine, isopropanolamine, di-isopropanolamine, tri(2-hydroxy-1-propyl amine, 2-amino-2-methyl-1-propanol, 2-amino-2-methyl-1,3-propanediol and 2-amino-2-hydroxymethyl-1,3-propanediol.

The polycondensates carrying amide functions are obtained by partial hydrolysis of polycondensates carrying nitrile functions, the hydrolysis conditions selected being those conventionally employed for the preparation of amides from the corresponding nitriles.

The following non-limiting Examples are given to illustrate the present invention.

EXAMPLE 1

Preparation of a polycondensate having units of the following formula

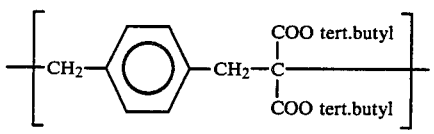

In a 1 liter round bottom flask fitted with a stirrer, a thermometer and a condenser there are introduced 54 g of di-tert.butyl malonate, 43.8 g of 1,4-dichloromethyl benzene, 100 ml of pure toluene and 29 g of BTEAC. After adjusting the temperature of this reaction mixture, with stirring at 500 rpm, to 50° C., there are introduced 500 ml of a 50 weight percent aqueous solution of NaOH.

Stirring is maintained for 2 hours at this temperature. The reaction mixture is then dissolved in 3 liters of a 1:1 mixture of acetone/water which is then stirred for 30 minutes. During this stirring operation an emulsion forms which is broken by adding 5 liters of water. After stirring the mixture the polycondensate precipitates and is then filtered on a Buchner and washed abundantly with water (5 times with 2 liters of water) until neutral pH, then with acetone (twice with 300 ml). The resulting polycondensate is dried under reduced pressure, providing 68 g of dry polymer; yield—69.5%.

EXAMPLE 2

Preparation of a polycondensate having units of the formula

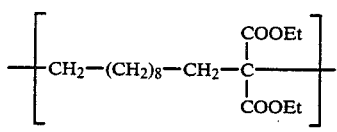

By operating in accordance with the procedures set forth in Example 1, there are introduced into a round bottom flask the following reactants:

48 g of diethyl malonate,
102 g of TBAHS,
400 ml of pure anhydrous toluene, and
94.8 g of 1,10-dibromo decane.

After the introduction of these reactants the mixture is heated with stirring to 40° C. for 10 minutes. There are then rapidly introduced into the heated mixture 200 g of powdered sodium hydroxide.

The reaction mixture is maintained at 60° C. for 4 hours with stirring, at which point the solution is poured into 400 ml of 35% HCl in a bath of 500 g of ice, all while maintaining the temperature lower than 15° C. After having verified that the pH of the reaction mixture is acidic the aqueous phase is decanted and extracted with 350 ml of toluene. The toluenic solution is washed three times with 350 ml of water until the pH of wash water is 7. The toluene is evaporated and the residue is taken up in a minimum of pure acetone. The polymer is precipitated by the addition of ice water; filtered off and then dried at 60° C. under reduced pressure. The polymer is obtained with a yield of 45.5% in the form of a white powder.

EXAMPLE 3

Preparation of a polycondensate having units of the following formula

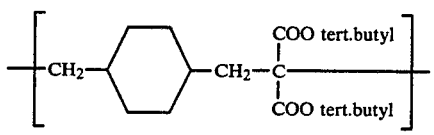

In a 100 ml round bottom flask, previously heated to 90° C., there are introduced:

6.4 (29.8 mmole) of di-tert.butyl malonate,
5.4 g (29.8 mmole) of 1,4-dichloromethyl cyclohexane,
10.2 g (29.8 mmole) of TBAHS and
20 g of anhydrous toluene.

The reaction mixture is stirred at 600–650 rpm, for 10 minutes at which point 10 g of powdered anhydrous sodium hydroxide are added thereto. The resulting mixture is maintained with stirring at 90° C. for 5 hours, cooled and then poured into a mixture of 30 g of 35% HCl with 50 g of ice, care being taken that the temperature remains lower than 10° C. The mixture is then extracted twice with 100 ml of toluene and the organic layers are washed three times with 100 ml of water. After drying the organic solution on sodium sulfate, the solvent is evaporated in a rotating evaporator.

The polymer is isolated with a yield of 80%.

EXAMPLE 4

Preparation of a polycondensate having units of the following formula

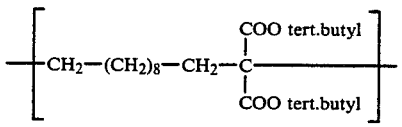

In a φml round bottom flask, heated to 60° C., there are introduced:

1.51 g (7 mmole) of di-tert.butyl malonate,
2.38 g (7 mmole) of 1,10-dibromo decane,
2.21 g (7 mmole) of TBAHS and 12 g of anhydrous toluene.

The mixture is stirred at a speed of 500 rpm and at a temperature 60° C. for 10 minutes at which point 20 g of a 50% aqueous solution of sodium hydroxide are introduced therein. The resulting reaction mixture is maintained at this temperature, with stirring, for 6 hours and then poured into a mixture of 20 g of ice and 30 ml of 35% HCl. Again, care is taken to insure that the temperature remains lower than 20° C. The organic layers are decanted and the aqueous layers are extracted twice with 30 ml of toluene. The combined organic layers are washed with water until neutral and then dried on sodium sulfate. The toluene is evaporated with a rotating evaporator. The crude polymer is taken up in a minimum of acetone, then precipitated in 50 ml of water in the form of a white powder.

Yield: 77%.

EXAMPLE 5

Preparation of a polycondensate having units of the following formula

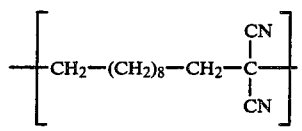

In a 1 liter round bottom flask fitted with a stirrer, a thermometer and a condenser there are introduced 5 g (75 mmole) of malonitrile, 25.5 g (75 mmole) of TBAHS, 14.75 g (75 mmole) of 1,10-dibromodecane and 100 g of toluene. The resulting reaction mixture is stirred vigorously for 10 minutes at a speed of 500 rpm and at ambient temperature at which point 50 g of NaOH in flake form are introduced therein.

Since reaction is exothermic, the reaction mixture is cooled and maintained at a temperature of 60° C. for 4 hours. The polymer is isolated in the form of a brown precipitate which is washed with water.

Yield: 70%.

EXAMPLE 6

Preparation of a polycondensate having units of the following formula

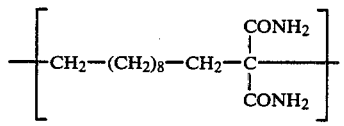

In a round bottom flask there are introduced 3.8 g of the polycondensate prepared in accordance with Example 5 above to which are added initially 7.5 ml of $H_2O_2$ at 110 volumes and then 10 ml of ethanol and 7.5 ml of 6N NaOH. The resulting mixture is then heated to 50° C. with stirring for 3 hours. After cooling, water is added to the mixture and the expected polycondensate is isolated in the form of a yellowish powder.

Yield: 20%.

EXAMPLE 7

Preparation of a polycondensate having units of the following formula

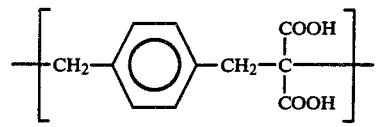

A. In a 1 liter round bottom flask fitted with a stirrer, a thermometer and a condenser, there are introduced 54 g of pure di-tert.butyl malonate, 43.8 g of 1,4-dichloromethyl benzene, 100 ml of pure toluene and 29 g of BTEAC.

After heating the resulting mixture, with stirring at 500 rpm, to 50° C. there are introduced 500 ml of a 50 weight percent aqueous solution of NaOH.

Stirring is maintained for two hours at this temperature.

The reaction mixture is then taken up in 3 liters of a 1:1 acetone:water mixture and the whole is stirred for about one-half hour. In the course of stirring an emulsion is formed which is broken by adding 5 liters of water. After stirring the mixture the polycondensate precipitates and is filtered off under a vacuum. The polycondensate is abundantly washed initially with water (5 times with 2 liters of water) until the pH is neutral and then with acetone (twice with 300 ml).

The polycondensate is then dried under a vacuum at 50° C. until constant weight.

Yield: 69.5% (dry weight: 68 g).

B. In a 1 liter round bottom flask fitted with a stirrer and an ampoule for introducing solids therein there are introduced 200 ml of pure anhydrous trifluoroacetic acid and then slowly 50 g of the polycondensate obtained in part A above in 40 minutes with stirring.

The resulting mixture is stirred for 4 hours, then diluted by the addition of 800 ml of water and finally filtered under a vacuum on fritted glass. The product is then washed abundantly with water until the pH of the filtrate is neutral.

The product is dried under a vacuum until constant weight at a temperature of about 50° C., thus providing 32 g of the expected product.

Yield: about 100%.

EXAMPLE 8

Preparation of a polycondensate having units of the following formula

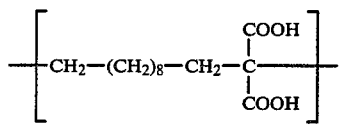

A. By operating in accordance with the procedures set forth in Example 7 A, there are introduced into a round bottom flask the following reactants:
  48 g of diethyl malonate,
  102 g of tetrabutylammonium hydrogen sulfate (TBAHS),
  400 ml of pure anhydrous toluene, and
  94.8 g of 1,10-dibromo decane.

After the introduction of the reactants the mixture is heated with agitation at 40° C. for 10 minutes, at which point 200 g of sodium hydroxide in flake form are rapidly introduced therein.

The reaction mixture is maintained at 60° C. for 4 hours with stirring.

The solution is then poured into 400 ml of 35% HCl in a bath of 500 g of ice, all while maintaining the temperature lower than 15° C.

After having verified that the pH of the reaction mixture is acidic, the aqueous phase is decanted and extracted with 350 ml of toluene.

The toluenic solution is then washed three times with 350 ml of water until the wash waters have a pH of 7.

After evaporation of the toluene, the residue is taken up in a minimum of pure acetone and a precipitate is obtained by the addition of ice water, thereby recovering the supernatant fatty phase which is dried at 60° C. using a blade pump.

The polymer is thus obtained in the form of a white precipitate.

Yield: 45.5%.

B. In a round bottom flask there are introduced 25 g of the polycondensate obtained in part A above to which are added 100 g of 20% NaOH.

The resulting mixture is then brought to reflux for 24 hours.

After addition of 100 ml of water the resulting mixture is again brought to reflux for 3 hours, cooled and then poured over 100 g of ice and 60 ml of concentrated HCl, while maintaining the temperature thereof lower than 10° C. A yellowish product is recovered by filtration and redissolved in a minimum of acetone. The desired polycondensate is then precipitated with water and isolated in the form of a white precipitate.

Yield: 80%.

EXAMPLE 9

Preparation of a polycondensate having units of the following formula

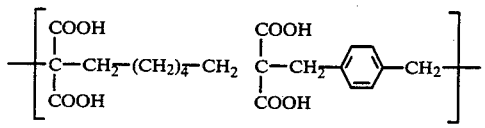

The following reactants are introduced into a 2-liter reaction:

40 g of diethyl malonate,
84.9 g of tetrabutylammonium hydrogen sulfate (TBAHS),
300 ml of anhydrous toluene,
23.2 g of 1,6-dichlorohexane,
17.5 g of 1,4-dichloroxylene.

After introduction of the reactants, the mixture is heated with stirring at 40° C. for 15 minutes at which point there are introduced, in a single charge, 150 g of NaOH in flake form.

The temperature of the reaction mixture rises to 80° C. and it is then cooled to 60° C. and maintained at this temperature for 5 hours.

750 ml of water are added to the reaction mixture and the whole is brought to reflux for about 15 hours.

After cooling to ambient temperature, the aqueous phase and the intermediate oily phase are decanted. The two phases are then treated with 250 ml of methylene chloride and a solution of 10 g of sodium borohydride in 25 ml of water.

After stirring, the organic phase is decanted and treated and again with 250 ml of methylene chloride and a solution of 5 g of sodium borohydride in 12 ml of water.

After removal of the methylene chloride, the aqueous phase is slowly poured, with stirring, into a cooled mixture containing 300 g of crushed ice and 300 g of 35% HCl.

The precipitated polymer is recovered and washed twice, with stirring, with 500 ml of water.

The expected polymer is then dried under a vacuum at 50° C. until constant weight.

Yield: 46.4% (22.5 g). Absolute viscosity in a 5% methanol solution at 25° C.=0.69 centipoise.

EXAMPLE 10

Preparation of a polycondensate having units of the following formula

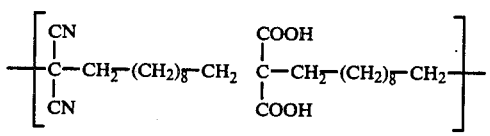

Into a 500 cm³ round bottom flask fitted with a stirrer, a thermometer and a condenser, there are introduced 21.6 g of di-tert.butyl malonate, 3.3 g of malodinitrile and 45 g of 1,10-dibromodecane, 200 ml of toluene and 50.9 g of TBAHS.

The resulting reaction mixture is then brought, with stirring at 500 rpm to a temperature of 50° C. at which point there are introduced 200 ml of a 50 weight percent aqueous solution of NaOH.

The intermediate polycondensate is isolated in accordance with the same procedures described in Example 7A.

The resulting intermediate polycondensate is then hydrolyzed in accordance with the procedures outlined in Example 7B thus providing 39.6 g of the expected polycondensate.

EXAMPLE A

A nail enamel is prepared by admixing the following components.

| | |
|---|---|
| Polycondensate obtained in accordance with Example 1 | 4 g |
| Nitrocellulose, ¼ sec. | 10 g |
| Ethyl alcohol | 3 g |
| Butyl alcohol | 3 g |
| Camphor | 4 g |
| Butyl acetyl ricinoleate | 8 g |
| Ethyl acetate | 14 g |
| Toluene | 23 g |
| Methyl ethyl ketone | 2 g |
| Bentone 27 (montmorillonite type clay-anti-sedimentation agent) | 1.4 g |
| Phosphoric acid | 0.01 g |
| Titanium oxide | 0.5 g |
| D and C Red 7, calcium lake | 0.3 g |
| D and C Red 6, barium lake | 0.2 g |
| Bismuth oxychloride | 0.8 g |
| Butyl acetate, sufficient amount for | 100 g |

In this Example the polycondensate obtained in accordance with Example 1 can be replaced by one of the polycondensates obtained according to Examples 2, 3 or 4.

EXAMPLE B

A body milk is prepared by admixing the following components:

| | |
|---|---|
| Diethyl hexyl adipate | 4.8 g |
| Stearic acid | 2.9 g |
| Lanolin alcohol ethoxylated with 5 moles of ethylene oxide | 0.5 g |
| Cetyl alcohol | 0.4 g |
| Glycerol stearate | 1 g |
| Triethanolamine | 0.95 g |
| Propylene glycol | 4.8 g |
| Polycondensate obtained in accordance with Example 2 | 2 g |
| Preservative | 0.2 g |
| Perfume | 0.1 g |
| Sterile, demineralized water, sufficient amount for | 100 g |

The polycondensate obtained in accordance with Example 2 can be replaced by that obtained in accordance with Examples 3 and 4.

EXAMPLE C

A hair setting lotion is prepared by admixing the following components:

| | |
|---|---|
| Polycondensate obtained in accordance with Example 8, 50% neutralized using 2-amino-2-methyl-1-propanol | 2.5 g |
| Ethanol | 50.0 g |
| Water, sufficient amount for | 100 g |

The polycondensate according to Example 8 can advantageously be replaced by the same amount of the polycondensate of Example 7.

Moreover, the neutralization agent can be replaced by NaOH.

EXAMPLE D

A hair rinse composition is prepared by admixing the following components:

| | |
|---|---|
| Polycondensate of Example 7 | 0.4 g |
| Polymer sold by GAF corporation under the tradename "GAFQUAT 755" | 0.5 g |
| | 0.5 g |
| Mixture of cetylstearyl alcohol and cetylstearyl alcohol oxyethylenated with 15 moles of ethylene oxide | 5 g |
| Triethanolamine, sufficient amount for pH = 8 | |
| Water, sufficient amount for | 100 g |

EXAMPLE E

A hair dye composition in the form of a gelifiable liquid is prepared as follows:

| Hair dye support or vehicle | |
|---|---|
| Oleyl alcohol glycerolated with 2 moles of glycerol | 20 g |
| Oleyl alcohol glycerolated with 4 moles of glycerol | 20 g |
| 2-butoxy ethanol | 8 g |
| Propylene glycol | 12 g |
| Ammonia - 22° Bé | 10 ml |
| Para aminophenol | 0.08 g |
| Metadiaminoanisole sulfate | 0.025 g |
| Resorcinol | 0.3 g |
| Metaaminophenol | 0.06 g |

| Hair dye support or vehicle | |
|---|---|
| Nitro paraphenylenediamine | 0.003 g |
| Paratoluylene diamine | 1.05 g |
| Hydroquinone | 0.17 g |
| Ethylenediamine tetraacetic acid | 3 g |
| Sodium bisulfite, d = 1.32 | 0.8 g |
| Water, sufficient amount for | 100 g |

To 50 g of the above support, there are mixed at the time of use 5 g of a 35% solution of the polycondensate of Example 7 and also 50 g of H$_2$O$_2$-20 volumes.

This resulting composition is then applied to the hair using a brush.

The composition is left on the hair for 30 minutes at which time the hair is rinsed. The thus treated hair is easy to comb, it has a silky touch and is shiny and full.

On deep chestnut colored hair a light chestnut coloration is obtained.

In this Example the polycondensate of Example 7 can be advantageously replaced by the same amount of the polycondensate of Example 8.

EXAMPLE F

A shampoo composition is prepared by admixing the following components:

| | |
|---|---|
| Triethanolamine lauryl sulfate | 10 g |
| Polycondensate of Example 7 | 1 g |
| 2-amino-2-methyl-1-propanol, sufficient amount for pH = 7 | |
| Water, sufficient amount for | 100 g |

EXAMPLE G

A shampoo composition is prepared by admixing the following components:

| | |
|---|---|
| Lauryl alcohol polyglycerolated with 4 moles of glycerol | 10 g |
| Polycondensate of Example 7 or 8 | 2 g |
| 2-amino-2-methyl-1-propanol, sufficient amount for pH = 7 | |
| Water, sufficient amount for | 100 g |

EXAMPLE H

A shampoo composition is prepared by admixing th following components:

| | |
|---|---|
| Lauryl alcohol polyglycerolated with 4 moles of glycerol | 10 g |
| Polycondensate of Example 7 | 1 g |
| Ammonia, sufficient amount for pH = 7 | |
| Water, sufficient amount for | 100 g |

EXAMPLE I

A hair lacquer is prepared by admixing the following components:

| | |
|---|---|
| Polycondensate of Example 7 | 2.5 g |
| 2-amino-2-methyl-1-propanol, sufficient amount for pH = 7 | |
| Ethanol, sufficient amount | 100 g |

The mixture is packaged in a flask provided with a pump.

EXAMPLE J

A nail enamel is prepared by admixing the following components:

| | |
|---|---|
| Nitrocellulose, ½ second | 10 g |
| Santolite MHP (aryl sulfonamide formaldehyde resin-modifying agent) | 4 g |
| Ethyl alcohol | 3 g |
| Butyl alcohol | 3 g |
| Polycondensate of Example 5 | 1 g |
| Camphor | 4 g |
| Butyl acetyl ricinoleate | 8 g |
| Ethyl acetate | 14 g |
| Toluene | 23 g |
| Methylethyl ketone | 2 g |
| Bentone 27 | 1.4 g |
| Phosphoric acid | 0.01 g |
| D and C Red 7 - calcium lake | 0.3 g |
| D and C Red 6 - barium lake | 0.2 g |
| Bismuth oxychloride | 0.8 g |
| Butyl acetate, sufficient amount for | 100 g |

In this Example the polycondensate of Example 5 be replaced by the same amount of the polycondensate of Example 6.

EXAMPLE K

A body milk is prepared by admixing the following components:

| | |
|---|---|
| Diethyl hexyl adipate | 4.8 g |
| Stearic acid | 2.9 g |
| Lanolin alcohol ethoxylated with 5 moles of ethylene oxide | 0.5 g |
| Cetyl alcohol | 0.4 g |
| Glycerol stearate | 1 g |
| Triethanolamine | 0.95 g |
| Propylene glycol | 4.8 g |
| Polycondensate of Example 7 | 0.5 g |
| Preservative | 0.2 g |
| Perfume | 0.1 g |
| Sterile demineralized water, sufficient amount for | 100 g |

EXAMPLE L

A beauty mask composition is prepared by admixing the following components:

| | |
|---|---|
| Polycondensate of Example 8, neutralized with 2-amino-2-methyl-1-propanol | 15 g |
| Propylene glycol | 5 g |
| Methyl parahydroxybenzoate, preservative | 0.2 g |
| Ethanol | 15 g |
| Kaolin | 10 g |
| Titanium oxide | 0.5 g |
| Triethanolamine lauryl sulfate | 6 g |
| Perfume | 0.15 g |
| Sterile, demineralized water, sufficient amount for | 100 g |

EXAMPLE M

A hair setting lotion is prepared by admixing the following components:

| | |
|---|---|
| Polycondensate of Example 9, 50% neutralized with 2-amino-2-methyl-1-propanol | 2.5 g |
| Ethanol | 50.0 g |
| Perfume | 0.05 g |
| Water, sufficient amount for | 100 g |

In this Example the polycondensate of Example 9 can be replaced by the same amount of the polycondensate of Example 10.

What is claimed is:

1. A process for setting the hair comprises applying thereto a hair setting amount of a composition which contains in an aqueous or alcohol solution wherein the alcohol is selected from the group consisting of ethanol and isopropanol from 0.5 to 25 percent by weight of a polycondensate having units of the formula

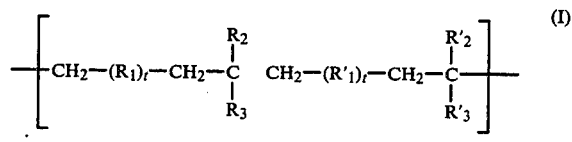

wherein
t is 0 or 1, and
when t=1, $R_1$ and $R'_1$ each idependently represent linear or branched alkylene having 1-38 carbon atoms; linear or branched alkylene having 1-38 carbon atoms and interrupted by —CONH— or —CO—; alkenyl or alkynyl having 2-18 carbon atoms; cycloalkylene having 5-6 carbon atoms; 1,4-dimethylene cyclohexane; phenylene; xylylene; diphenylene; diphenylene methane; 2,2-diphenylene propane; or a divalent radical of the formula

wherein n is 0-20 and R' represents hydrogen or methyl, and
$R_2$, $R'_2$, $R_3$ and $R'_3$ each independently represent —$COOR_4$, —CN, —$CONH_2$ or —$COCH_3$, wherein $R_4$ represents hydrogen, linear or branched alkyl having 1-18 carbon atoms or cycloalkyl having 5-6 carbon atoms.

2. A hair lacquer composition consisting essentially of a solution in an alcohol selected from the group consisting of ethanol and isopropanol, of from 0.2 to 8 percent by weight of a polycondensate having units of the formula

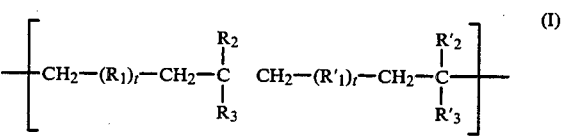

wherein
t is 0 or 1, and
when t=1, $R_1$ and $R'_1$ each independently represent linear or branched alkylene having 1-38 carbon atoms; linear or branched alkylene having 1-38 carbon atoms and interrupted by —CONH— or —CO—; alkenyl or alkynyl having 2-18 carbon atoms; cycloalkylene having 5-6 carbon atoms; 1,4-dimethylene cyclohexane; phenylene; xylylene; diphenylene; diphenylene methane; 2,2-diphenylene propane; or a divalent radical of the formula $-CHR'-O+C_2H_3(R')O\}_{\overline{n}}HCR'-$ wherein n is 0-20 and R' represents hydrogen or methyl, and $R_2$, $R'_2$, $R_3$ and $R'_3$ each independently represent $-COOR_4$, $-CN$, $-CONH_2$ or $-COCH_3$, wherein $R_4$ represents hydrogen, linear or branched alkyl having 1-18 carbon atoms or cycloalkyl having 5-6 carbon atoms, said alcohol being present in an amount from 6 to 30 weight percent and the remainder of said composition being a liquefied gaseous propellant under pressure, said propellant being selected from the group consisting of dichlorodifluoromethane, trichlorofluoromethane, nitrous oxide, $CO_2$ and a mixture thereof.

3. The composition of claim 2 wherein said polycondensate has a molecular weight between 400 and 100,000, measured by osmometry or by light diffusion method, or by size exclusion chromatography.

4. The composition of claim 3 wherein said polycondensate has a molecular weight between 1,000 and 30,000.

5. The composition of claim 3 wherein the polycondensate at least one of $R_2$, $R'_2$, $R_3$ and $R'_3$ represents a free carboxylic acid function, said function being neutralized in an amount between 10 and 100 percent by a organic or mineral base selected from the group cosisting of NaOH, KOH, ammonia, monoethanolamine, diethanolanolamine, triethanolamine, isopropanolamine, diisopropanolamine, tri(2-hydroxy-1-propyl) amine, 2-amino-2-methyl-1-propanol, 2-amino-2-methyl-1,3-propanediol and 2-amino-2-hydroxymethyl-1,3-propanediol.

* * * * *